(12) United States Patent
Ameri et al.

(10) Patent No.: US 8,583,242 B2
(45) Date of Patent: Nov. 12, 2013

(54) SUBCHOROIDAL RETINAL PROSTHESIS

(75) Inventors: Hossein Ameri, Alhambra, CA (US);
Mark S. Humayun, Glendale, CA (US);
James D. Weiland, Valencia, CA (US)

(73) Assignee: Doheny Eye Institute, Los Angeles, CA (US)

( * ) Notice: Subject to any disclaimer, the term of this patent is extended or adjusted under 35 U.S.C. 154(b) by 1166 days.

(21) Appl. No.: 12/348,860

(22) Filed: Jan. 5, 2009

(65) Prior Publication Data
US 2009/0177245 A1 Jul. 9, 2009

Related U.S. Application Data

(60) Provisional application No. 61/018,996, filed on Jan. 4, 2008.

(51) Int. Cl.
*A61N 1/32* (2006.01)
(52) U.S. Cl.
USPC .................................................... 607/54
(58) Field of Classification Search
USPC ........................................... 607/53, 54
See application file for complete search history.

(56) References Cited

U.S. PATENT DOCUMENTS

| 7,738,962 | B2 * | 6/2010 | Greenberg et al. | 607/53 |
| 2003/0028225 | A1 * | 2/2003 | Chow et al. | 607/54 |
| 2007/0142878 | A1 * | 6/2007 | Krulevitch et al. | 607/54 |

\* cited by examiner

*Primary Examiner* — Christopher D Koharski
*Assistant Examiner* — Frances Oropeza
(74) *Attorney, Agent, or Firm* — McDermott Will & Emery LLP

(57) ABSTRACT

Embodiments of the present disclosure are directed to utilization of one or more arrays that are placed under the choroid. In this approach, an array is placed under the choroid. To achieve this, a scleral incision can be made without cutting the underlying choroid or retina. The array can then be inserted into the space between the sclera and choroid and is pushed to the desired place. It is possible to make several of such scleral incisions in each quadrant of the eye to insert arrays of similar or different shapes into the subchoroidal space. Following insertion of the electrode array the scleral wound may be sutured around the cable to make the array and the eye more stable.

8 Claims, 4 Drawing Sheets

SUBCHOROIDAL RETINAL PROSTHESIS

RELATED APPLICATION

This application claims priority to U.S. Provisional Patent Application Ser. No. 61/018,996, entitled "Subchoroidal Retinal Prosthesis," filed 4 Jan. 2008, the entire contents of which are incorporated herein by reference.

BACKGROUND

In some situations, such as to overcome retinal damage or disease, it may be desired to stimulate the retina of the eye with electrical signals from electrodes. Prior art techniques for retinal stimulation have included the following:

Epiretinal prosthesis approaches and techniques, in which an array is placed over the retina and is fixed with a tack. The actual and potential challenges of these approaches and techniques can included various of the following: mechanical retinal damage, unequal distance of electrodes from the retina and providing small field of vision Subretinal prosthesis approaches and techniques, in which an array is placed under the retina. The actual and potential challenges of these approaches and techniques can include the following: very difficult surgical procedure with a high risk of serious complications, mechanical retinal damage and providing small field of vision Suprachoroidal prosthesis approaches and techniques, in which an array is placed in a scleral pocket. The actual and potential challenges of these approaches and techniques can include the following: low resolution vision due to large distance of the array from the retina and providing small field of vision Episcleral prosthesis approaches or techniques, in which an array is placed over the sclera. The actual and potential challenges for these approaches and techniques can include that because the array is so far from the retina it may only be able to provide a very low resolution vision.

What is desirable therefore are techniques and apparatus that address and overcome the disadvantages and challenges associated with prior art retinal stimulation techniques and apparatus.

SUMMARY

The present disclosure is directed to systems, methods, techniques, and apparatus useful for subchoroidal retinal prosthesis. Embodiments of the present disclosure can enable fixing of one of more electrode arrays under the choroid or a patient's eye, without the need for using any tack or adhesive materials. Embodiments of the present disclosure can also (or in substitution) allow stimulating a relatively large area of the retina by inserting multiple electrode arrays in the subchoroidal space.

One aspect of the present disclosure includes a subchoroidal array prosthesis system including one or more subchoroidal electrode arrays configured and arranged for placement adjacent to (or under) the choroid of an eye, and one or more connecting cables configured and arranged to connect the one or more subchoroidal electrode arrays to a control unit. The system can also include one or more electronic components, e.g., chips, connected to the arrays either directly or indirectly. A cable may be present to interface with systems/components outside of the eye of the patient.

A further aspect of the present disclosure is directed to a method of placing a subchoroidal array under a choroid of a patient's eye. The method can include making a scleral incision without cutting the underlying choroids or retina. A subchoroidal electrode array can then be inserted into the space between the sclera and the choroids. The subchoroidal array can then can be positioned at a desired location.

Other features and advantages of the present disclosure will be understood upon reading and understanding the detailed description of exemplary embodiments, described herein, in conjunction with reference to the drawings.

BRIEF DESCRIPTION OF DRAWINGS

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 4A depicts a fundus photograph of a rabbit showing an implanted electrode array of an embodiment of the present disclosure in the subchoroidal space; FIG. 4B depicts a fundus photograph of a rabbit, showing two implanted dummy arrays in the subchoroidal space.

Figure 1A:
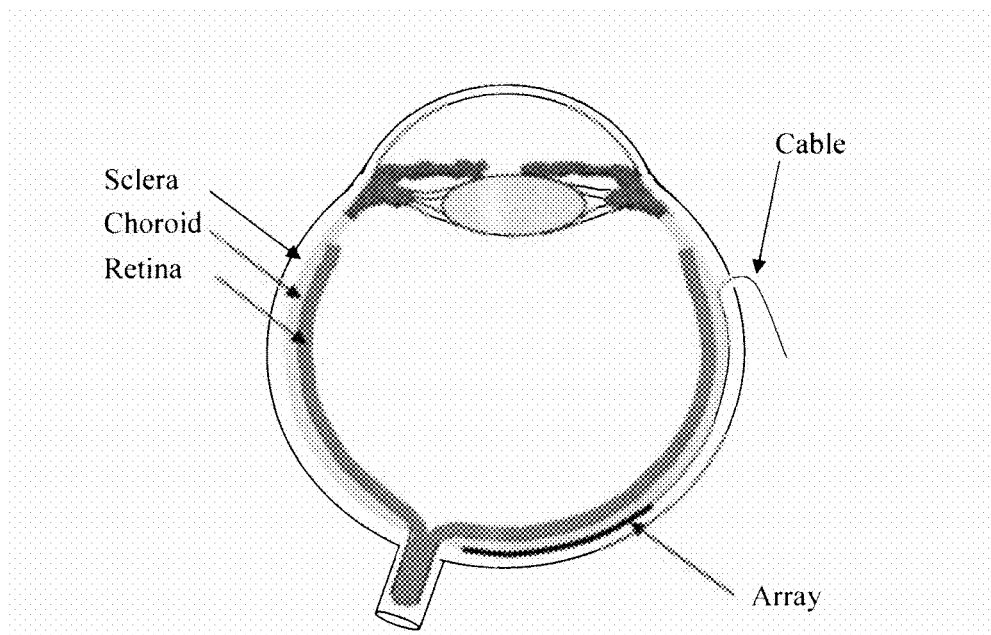
FIG. 1A depicts the location of electrode arrays and cables in a side view of a cross section of the an eye, in accordance with an embodiment of the present disclosure.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION

Embodiments of the present disclosure are directed to utilization of one or more arrays that are placed under the choroid. To achieve this, a scleral incision can be made without cutting the underlying choroid or retina.

FIG. 1A depicts location of electrode arrays and cables in side view of a cross section of the an eye, in accordance with an embodiment of the present disclosure. As shown in FIG. 1A, an array can then be inserted into the space between the sclera and choroid and is pushed to the desired place. The individual electrodes can be as known in the art, and can include suitable metals and alloys, e.g., platinum and/or iridium.

Figure 1B:
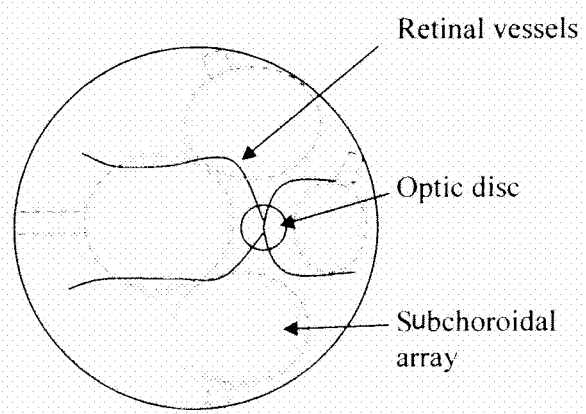
FIG. 1B depicts a corresponding front view of the fundus of the eye shown for FIG. 1A; This is a schematic drawing and the arrays may not be visible through the fundus.

FIG. 1B depicts a corresponding front view of the fundus of the eye shown for FIG. 1A. As shown in FIG. 1B, it is possible to make several of such scleral incisions in each quadrant of the eye to insert arrays of similar or different shapes into the subchoroidal space. Following insertion of the electrode array the scleral wound may be sutured around the cable to make the arrays more stable and to prevent any complication arising from a scleral defect.

Figure 2:
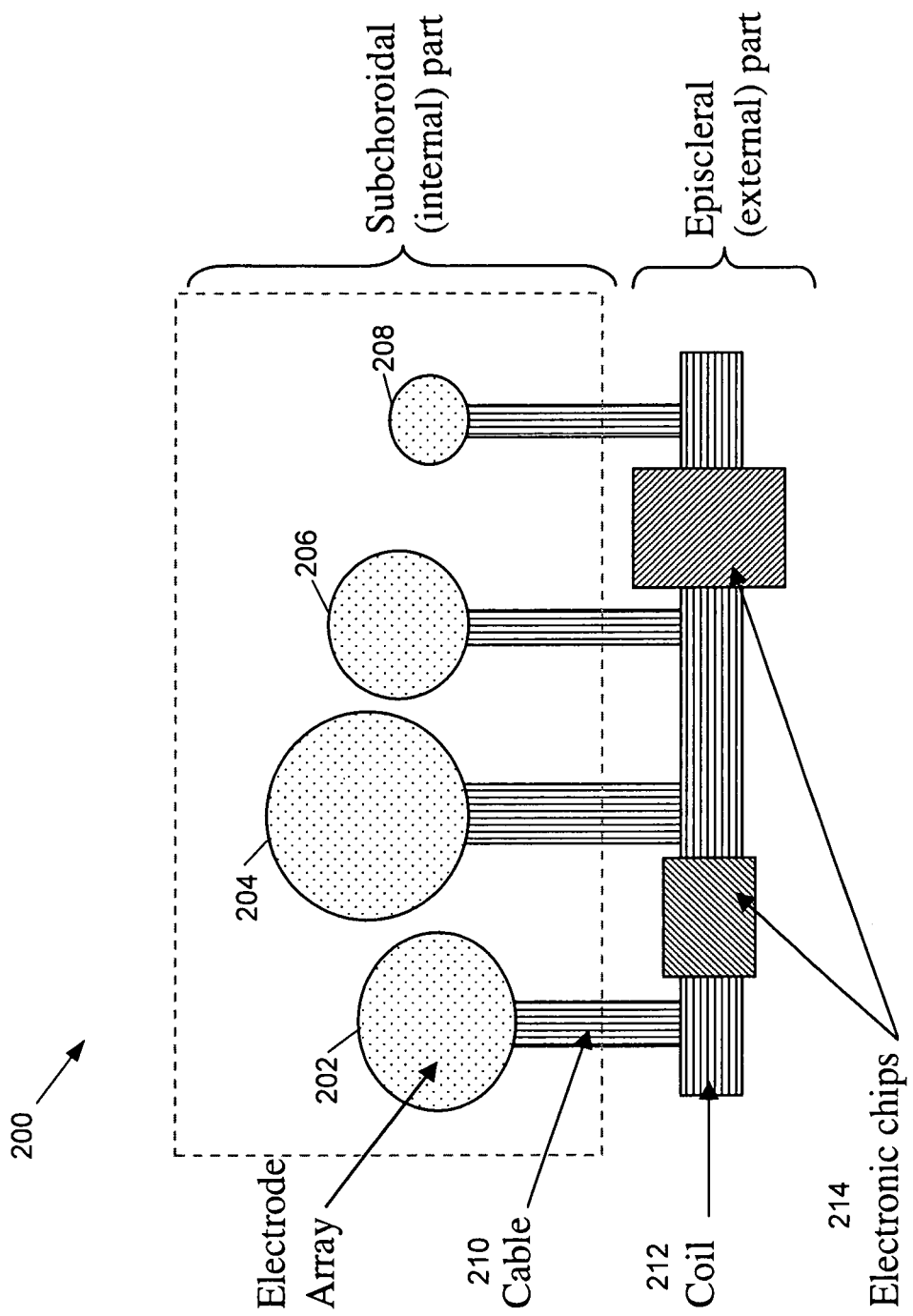
FIG. 2 depicts a schematic view of an exemplary subchoroidal retinal prosthesis according to the present disclosure.

FIG. 2 depicts a schematic view of an exemplary subchoroidal retinal prosthesis 200 according to the present disclosure. The prosthesis can include a number of electrode arrays 202-208 connected by cables 210 to a coil 212 and electronic chips (or components) 214. As shown in FIG. 2, more than one array may be used for the prosthesis 200, and each such array can have a variety of sizes and shapes, as desired.

As shown in FIG. 2 (and also FIG. 1B), multiple subchoroidal arrays can be located at desired locations of the eye. For embodiments having multiple electrode arrays, each array can be inserted (inserted into the space between the sclera and choroid) by a separate entry point/incision, though this not necessary for all applications. It is possible to make several of such scleral incisions in each quadrant of the eye to insert arrays of similar or different shapes into the subchoroidal space, e.g., as shown in FIG. 1B.

In exemplary embodiments, the arrays 202-208 can be fabricated from soft materials (e.g., flexible substrates such as polyimide) and can uniformly conform to the curvature of the eyeball; hence, all the electrodes of the arrays can have almost equal distance from the retina. This distance is determined by the thickness of the choroid, which is typically about 150μ.

With further reference to FIG. 2, in exemplary embodiments one or more subchoroidal arrays may be used in combination with one or more epiretinal or subretinal arrays (not shown). For example, while epiretinal or subretinal arrays can provide a high resolution central vision, the subchoroidal array(s) may/can provide a very large peripheral vision/enhancement.

In exemplary embodiments, a return electrode may be placed in the subchoroidal, episcleral, or subretinal space in the other side of the eyeball, or it may be placed in the vitreous cavity. Additionally, in exemplary embodiments, the subchoroidal array may serve or function as a return and/or recording array for a epiretinal and/or subretinal stimulating array. Suitable examples of return arrays are disclosed in related international application serial number PCT/US2006/017282, filed 4 May 2006, entitled "Retinal Prosthesis with Separate Central Electrode Array and Peripheral Electrode Array"; additional related prosthesis features are described in related U.S. patent application Ser. No. 09/783,236 filed 13 Feb. 2001, and entitled "Implantable Retinal Electrode Array Configuration for Minimal Retinal Damage and Method of Reducing Retinal Stress"; U.S. patent application Ser. No. 10/112,801, filed 28 Mar. 2002, entitled "Variable Pitch Electrode Array,"; and U.S. patent application Ser. No. 11/413,689, filed 28 Apr. 2006, entitled "Flexible Circuit Electrode"; the entire contents of all of which application are hereby incorporated herein by reference.

Figure 3:
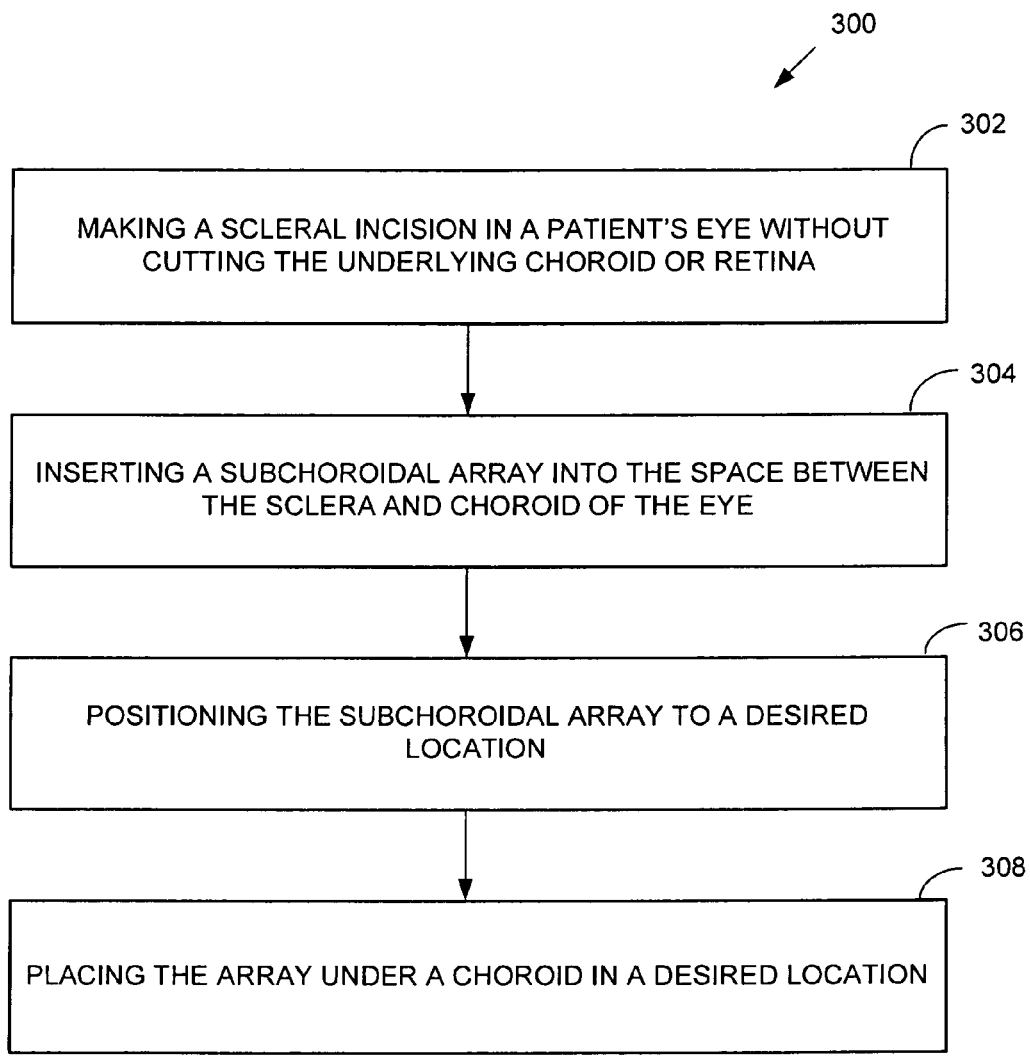
FIG. 3 depicts a method according to an exemplary embodiment of the present disclosure.
Figure 4A:
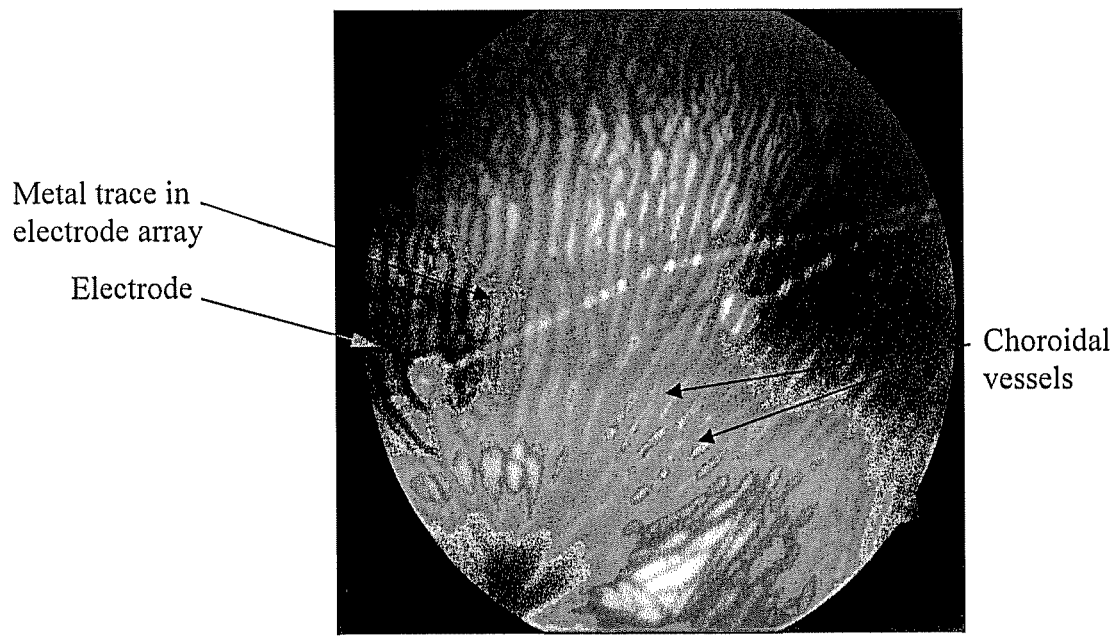
FIGS. 4A-4B depict fundus photographs (originally in color—with blood vessels indicated by red)
Figure 4B:
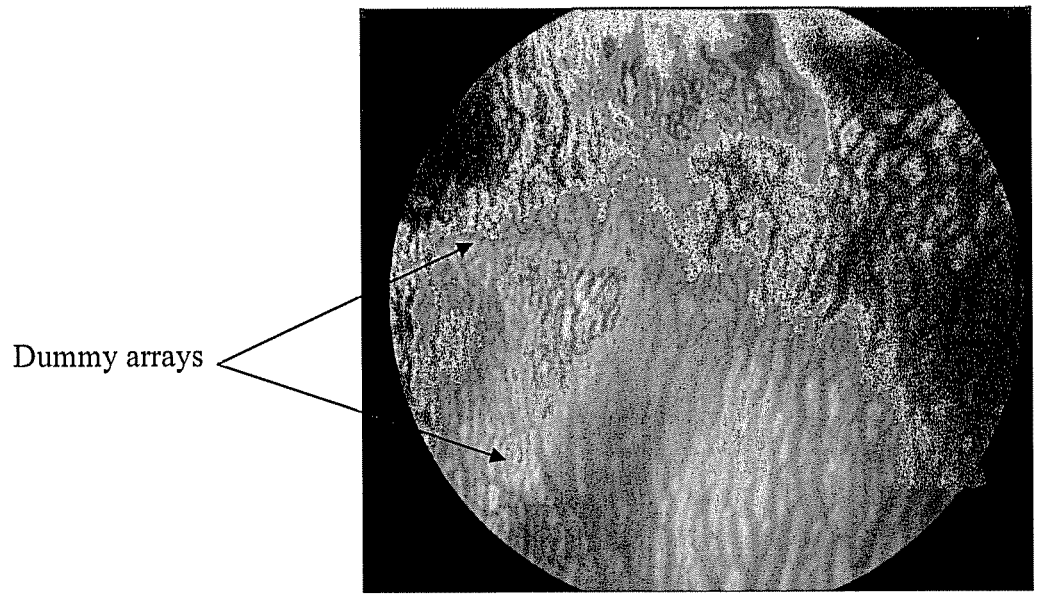

FIG. 3 depicts a method 300 of placing a subchoroidal array under a choroid, according to an exemplary embodiment of the present disclosure. A scleral incision can be made without cutting the underlying choroid or retina, as described at 302. A subchoroidal array can be inserted into the space between the sclera and the choroid, as described at 304.

Continuing with the description of method 300, the subchoroidal array can be positioned, e.g., pushed, to a desired location, as described at 306. And, the array can consequently be placed under a choroid in a desired location, as described at 308.

Accordingly techniques of the present disclosure can provide one or more of the following advantages, compared to the current evaluation methods mentioned above. Unlike in epi- and sub-retinal methods there is a very low risk of mechanical retinal damage because the array is not in contact with the retina and there is no need to use a tack or any adhesive material to fix the array onto the retina. Thus, the risk of electrical retinal damage may be less than epi- and sub-retinal approaches. As the choroid is very vascular and dissipates the heat, a result of utilizing embodiments of the present disclosure is that the risk of thermal retinal damage is less than epi- and sub-retinal approaches. Moreover, the distance between the array and the retina is more predictable than other approaches. This is an advantage over all other prior art methods.

Unlike all other prior art methods, techniques of the present disclosure can afford the potential to cover almost all the corresponding retina to give a close to normal field of vision. This can be achieved best by inserting multiple arrays from different quadrants. As a consequence, surgical procedure for implantation of prosthesis according to the present disclosure can be relatively easy and safe, compared to prior art techniques.

While certain embodiments have been described herein, it will be understood by one skilled in the art that the methods, systems, and apparatus of the present disclosure may be embodied in other specific forms without departing from the spirit thereof. For example, while certain geometric shapes have been shown and described specifically for exemplary embodiments of subchoroidal arrays, others may be used within the scope of the present disclosure.

Accordingly, the embodiments described herein are to be considered in all respects as illustrative of the present disclosure and not restrictive.

What is claimed:

1. A subchoroidal retinal prosthesis system comprising:
   a subchoroidal part including (i) one or more subchoroidal electrode arrays configured and arranged for placement adjacent to the choroid of an eye, and (ii) one or more connecting cables configured and arranged to connect the one or more subchoroidal electrode arrays to a control unit; and
   an episcleral part including one or more coils connecting respective cables connected to each of the one or more subchoroidal electrode arrays.

2. The system of claim 1, wherein the one or more connecting cables comprise a return electrode connected to the one or more subchoroidal arrays.

3. The system of claim 1, wherein the one or more subchoroidal arrays comprise four arrays.

4. The system of claim 1, further comprising a subchoroidal part and a epiretinal part.

5. The system of claim 1 wherein the episcleral part comprises one or more electronic chips connected to the one or more coils.

6. The system of claim 1, wherein the subchoroidal array is a stimulating array.

7. The system of claim 1, wherein the subchoroidal array is a return electrode array.

8. The system of claim 1, wherein the subchoroidal array is a recording electrode array.

* * * * *